United States Patent [19]
LeFebvre et al.

[11] Patent Number: 5,977,339
[45] Date of Patent: Nov. 2, 1999

[54] METHODS AND COMPOSITIONS FOR DIAGNOSING LYME DISEASE

[75] Inventors: Rance B. LeFebvre, Davis, Calif.; Guey-Chen Perng, San Gabriel, Calif.

[73] Assignee: The Regents of the University of California, Oakland, Calif.

[21] Appl. No.: 08/785,190

[22] Filed: Jan. 17, 1997

Related U.S. Application Data

[60] Continuation of application No. 08/180,586, Jan. 12, 1994, abandoned, which is a division of application No. 07/720,589, Jun. 28, 1991, Pat. No. 5,324,630.

[51] Int. Cl.$^6$ .................................................. C07H 21/04
[52] U.S. Cl. .................... 536/24.32; 536/23.1; 536/23.7; 536/24.1; 435/7.2; 435/69.3; 435/172.1; 435/320.1; 424/184.1
[58] Field of Search .................................. 435/7.2, 320.1, 435/172.1, 69.3; 536/23.1, 23.7, 24.1, 24.32; 424/184.1

[56] References Cited

U.S. PATENT DOCUMENTS 5,217,872   6/1993   Dorward et al. .

FOREIGN PATENT DOCUMENTS

WO 90/04411   5/1990   WIPO .

OTHER PUBLICATIONS

Perng et al. Infect. Immun. 1991 59(6): 2070–2074.
Lefebvre et al. J. Clin. Microbiol. 1990. 28(7): 1673–1675.
Cover of J. Clin. Micro. (Jul. 1990 issue), Jun. 26, 1990.
Craft et al. (1986) Clin. Invest. 78:934–938 "Antigens of *Borrelia burgdorferi* Recognized during Lyme Disease".
Grodzicki et al. (1988) J. Infect. Dis. 157:790–797 "Comparison Assay of Immunoblotting and Indirect Enzyme–Linked Immunoadsorbent Assay Using Different Antigen Preparations for Diagnosing Early Lyme Disease".
Nadal et al. (1989) Pediatri. Res. 26:377–382 "Immunoblot Analysis Of Antibody Binding to Polypeptides of *Borrelia burgdorferi* in Childeren with Different Clinical Manifestations of Lyme Disease".
LeFebvre et al. (1990) J. Clin. Microbiol. 28:1673–1675 "The 83–Kilodalton Antigen of *Borrelia burgdorferi* Which Immunoadsorbent Assay Using Different Antigen Preparations for Diagnosing Early Lyme Disease".
Perng et al. (1991) Infect. Immun. 59:2070–2074 "Further Characterization of a Potent Immunogen and the Chromosomal Gene Encoding It in the Lyme Disease Agent, *Borrelia burgdorferi*".
Harlow et al. "Antibodies: A Laboratory Manual," 1988 by Cold Spring Harbor (New York), see pp. 141, 142, 516.

*Primary Examiner*—James C. Housel
*Assistant Examiner*—Jennifer Graser
*Attorney, Agent, or Firm*—Townsend and Townsend and Crew LLP

[57] ABSTRACT

A chromosomal gene of *Borrelia burgdorferi* which encodes a conserved antigen of approximately 79 kD has been isolated and sequenced. The chromosomal gene, the gene product, and antibodies to the gene product may be used in diagnostic methods for the detection of *Borrelia burgdorferi* infection. The antigen and fragments thereof are suitable for use in vaccine compositions and methods.

4 Claims, 5 Drawing Sheets

METHODS AND COMPOSITIONS FOR DIAGNOSING LYME DISEASE

This is a continuation of Ser. No. 08/180,586, filed Jan. 12, 1994, now abandoned, which is a divisional of Ser. No. 07/720,589, filed Jun. 28, 1991, now U.S. patent Ser. No. 5,324,630 which issued Jun. 28, 1994.

BACKGROUND OF THE INVENTION

1. Field of the Invention

Lyme disease was first described in the late 1970's as a unique grouping of arthritic symptoms in patients from Lyme, Conn. Subsequent investigation demonstrated that the disease is caused by infection with *Borrelia burgdorferi*, a spirochete, following exposure to deer (ixodid) ticks. It is now known that lyme disease in humans is a multi-systemic disorder characterized by dematologic, rheumatologic, cardiac, and neurologic manifestations.

While several isolates of *Borrelia burgdorferi* from North America and Europe have been characterized at both the genetic and antigenic level, the unequivocal diagnosis of lyme disease remains problematic. Isolation and cultivation of borrelia from infected patients is difficult and not practical for routine diagnosis. Immunological and genetic detection methods have not become generally available, at least in part because the known major antigens of *Borrelia burgdorferi* have previously been thought to be coded on linear plasmid and have demonstrated significant antigenic variation with regard to the level of expression and molecular weight. There have also been reports of serological cross-reactivity with related human pathogens, such as *B. hermsii* (the causative agent of tick-born relapsing fever) and *Treponema palladium* (the causative agent of syphilis).

It would therefore be desirable to provide improved methods for diagnosing lyme disease and in particular for unequivocally determining the presence of *Borrelia burgdorferi* in patient samples. To provide such methods, it would be desirable to identify genetic and antigenic information which is widely conserved among *Borrelia burgdorferi* strains and which can be used in a variety of detection protocols. More specifically, it would be desirable to identify a conserved chromosomal gene which encodes a major antigenic protein, where the gene can serve as the basis for genetic screening assays and the antigen can serve as the basis for immunologic screening assays.

2. Description of the Background Art

Immunochemical analyses of *Borrelia burgdorferi* have revealed the presence of several immunodominant antigens that are recognized during the described stages of human infection. (Craft, et al. (1986). Clin. Invest. 78: 934–938; Grodzicki, et al. (1988) J. Infect. Dis. 157: 790–797; Nadal, et al. (1989) Pediatr. Res. 26: 377–382) One of the immunodominant antigens was reported to have a molecular weight of approximately 83 kD. No description or characterization of the gene encoding this antigen had been reported prior to the work which is the subject of the present application. The data included in the Experimental section hereinafter was reported in LeFebvre et al. (1990) J. Clin. Microbiol. 28: 1673–1675 and in Perng et al. (1991) Infect. Immun. 59: 2070–2074.

SUMMARY OF THE INVENTION

The methods and compositions of the present invention are based on the discovery that an approximately 79 kilodalton (kD) immunodominant antigen of *Borrelia burgdorferi* is encoded by a chromosomal gene which is widely conserved among strains throughout Europe and North America. Based on this discovery, the present invention provides screening assays for *Borrelia burgdorferi* infection, where the assays detect the presence of the chromosomal gene, the gene product (79 kD antigen), or antibodies to the 79 kD antigen, in a patient sample.

The present invention also provides isolated polynucleotides which encode the approximately 79 kD antigen or fragments thereof, as well as oligonucleotides capable of hybridizing under stringent conditions to the chromosomal gene. The oligonucleotides may be labeled for use in hybridization assays or may be present as primer pairs for use in polymerase chain reaction assays.

The present invention further provides diagnostic kits which contain a reagent capable of binding to the gene, gene product (antigen), or antibodies to the antigen under conditions which permit detection of binding. The kits will further contain instructions which set forth the corresponding detection protocol, such as hybridization assays, polymerase chain reaction assay, or immunoassay.

The present invention still further comprises isolated and optionally purified polypeptides which comprise a sequence analogous to at least six contiguous amino acids of the approximately 79 kD antigen. Such polypeptides may be produced by expression of a heterologous gene in cultured cells and will usually be reactive with antibodies produced by a host in response to infection by *Borrelia burgdorferi*. Preferably, the polypeptides will be capable of eliciting a protective immunity when administered to a susceptible host.

Vaccine compositions according to the present invention will comprise a polypeptide which is immunologically cross-reactive with the conserved 79 kD immunodominant antigen. The polypeptide will be present in a physiologically acceptable carrier in an amount effective to elicit protective immunity when administered to a susceptible host. The polypeptide may comprise substantially the entire 79 kD antigen, or may be a portion thereof. Frequently, the polypeptide will be produced by expression in a heterologous gene in cultured cells.

The present invention further comprises monospecific antibodies for the conserved 79 kD antigen of *Borrelia burgdorferi*. The monospecific antibodies may be monoclonal or polyclonal.

DESCRIPTION OF THE PREFERRED EMBODIMENT

Figure 1:
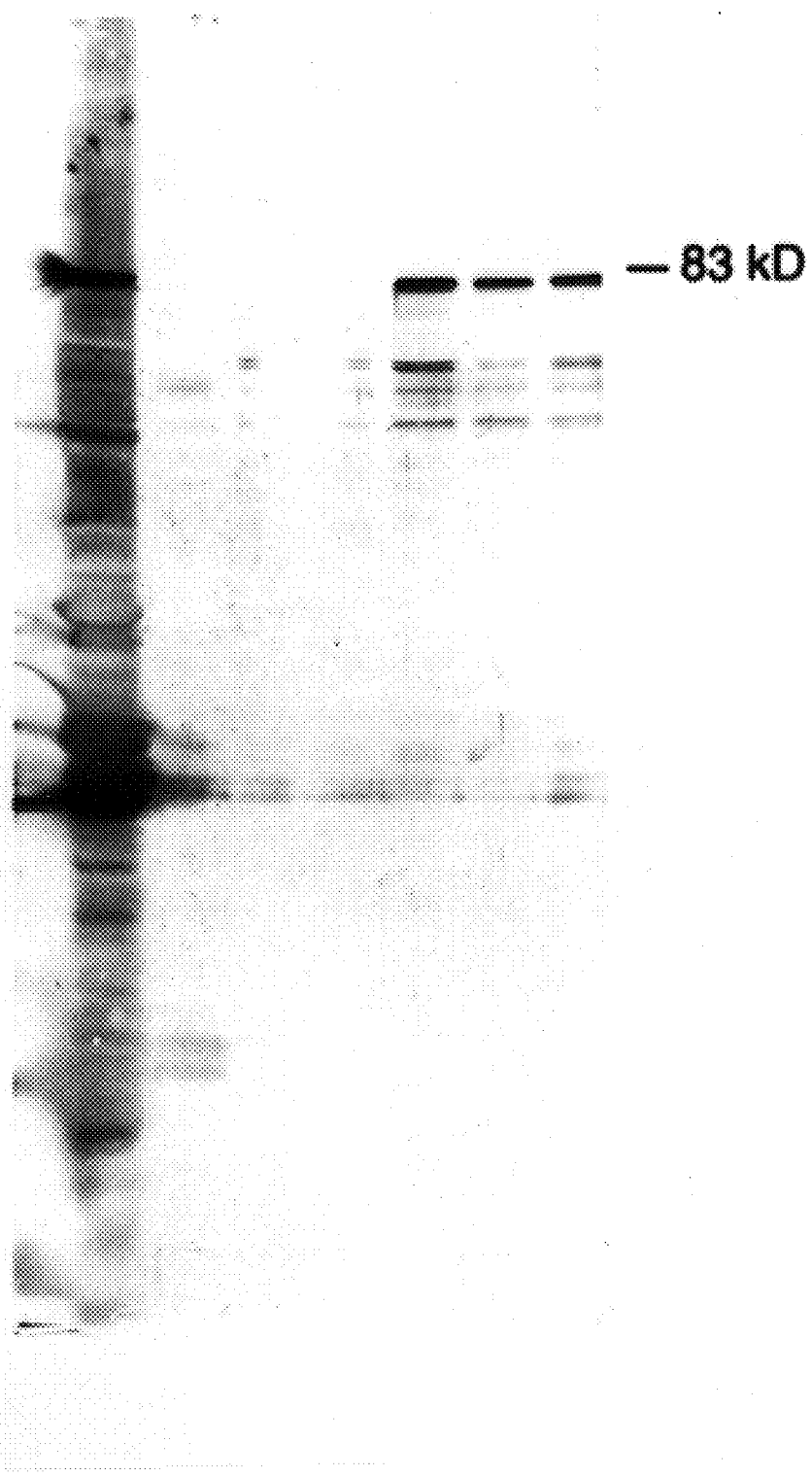
FIG. 1 is an immunoblot demonstrating the reactivity of the approximately 79 kD antigen to rabbit antiserum raised against whole-cell *Borrelia burgdorferi*.

The present invention provides novel compositions and methods for diagnosing, treating, and vaccinating against infection by *Borrelia burgdorferi*, the spirochete which causes Lyme disease in humans. The invention is based, in part, on the discovery of a widely conserved approximately 79 kilodalton (kD) immunodominant antigen which is encoded by a chromosomal gene. As discussed above, the existence of the chromosomal gene encoding an immunodominant antigen is surprising since previous genes encoding major antigens of *Borrelia burgdorferi* were believed to be located on linear plasmids, and would therefore not be expected to be as widely conserved as chromosomal genes.

The present invention provides a complete sequence of the chromosomal gene encoding the 79 kD antigen as well as the corresponding amino acid sequence of the antigen itself. Both the polynucleotide and the sequence and the amino acid sequence are set forth in SEQ ID NO: 1 and SEQ ID NO: 2, respectively. The 79 kD antigen gene is contained within a 2.5 kilobase pair (kbp) FoKI fragment of the chromosomal DNA of *Borrelia burgdorferi* reference strain B31, which is available from the American Type Culture Collection, 12301 Parklawn Drive, Rockville, Md. 20852, under the designation ATCC 35210.

It will be appreciated that the DNA sequence set forth in SEQ ID NO: 1 represents the particular allele which is present in the reference strain B31 and that other alleles will exist in nature. The compositions of the present invention may be derived from such other alleles and from the nucleic acid and amino acid sequences of such alleles according to the general methods as described hereinafter.

In accordance with the present invention, nucleic acid sequences encoding the conserved 79 kD antigen have been isolated and characterized. An isolated nucleic acid is one which has been removed from its natural chromosomal location. Isolated nucleic acids may be produced by excision from the chromosomal DNA of cultured *Borrelia burgdorferi* cells, e.g., using restriction enzymes. Alternatively, the isolated nucleic acids may be produced by the synthesis techniques set forth hereinbelow.

Isolated nucleic acid sequences, including polynucleotides and oligonucleotides, encoding the antigen and portions thereof may be expressed in cultured cells to provide isolatable quantities of polypeptides displaying biological (e.g. immunological) properties of the naturally occurring 79 kD antigen. Other useful nucleic acids are substantially homologous to the sequences encoding the antigen, can be either natural or synthetic. Such homologous nucleic acids may find use as probes or primers for locating or characterizing natural or synthetic nucleic acids encoding the 79 kD antigen.

Substantial homology of a nucleic acid sequence means either that (a) there is greater than about 65%, typically greater than about 75%, more typically greater than about 85%, preferably greater than about 95%, and more preferably greater than about 98% homology with a compared segment of at least about 10 contiguous nucleotides or (b) the homologous nucleic acid sequence will hybridize to the compared sequence or its complementary strand under stringent conditions of the temperature and salt concentration. These stringent conditions will generally be a temperature greater than about 22° C., usually greater than about 30° C. and more usually greater than about 45°, and a salt concentration generally less than about 1 M, usually less than about 500 mM, and preferably less than about 200 mM. The combination of temperature and salt concentration is more important in defining stringency than either the temperature or the salt concentration alone. Other conditions which affect stringency include GC content of the compared sequence, extent of complementarity of the sequences, and length of the sequences involved in the hybridization, as well as the composition of buffer solution(s) used in the hybridization mixture. These and other factors affecting stringency are well described in the scientific and patent literature.

Nucleic acids according to the present invention can be synthesized based on the DNA sequence set forth in SEQ ID NO: 1 using well known synthesis techniques. For example, short, single-stranded DNA fragments (oligonucleotides) may be prepared by the phosphoramadite method described by Beaucage and Carruthers (1981) Tett. Lett. 22: 1859–1862. A double-stranded fragment may then be obtained by either synthesizing the complementary strand and annealing the strands together under appropriate conditions or by adding the complementary strand using DNA polymerase and an appropriate primer sequence.

Polymerase chain reaction techniques may also be used for the production of probes and/or the amplification of polynucleotides for synthetic purposes. Suitable primer pairs for use in polymerase chain reaction techniques may be obtained based on the DNA sequence of SEQ ID NO: 1. See, Innis et al., Ed., *PCR Protocols,* Academic Press, New York, 1990, the disclosure of which is incorporated herein by reference.

Natural or synthetic DNA fragment encoding the 79 kD antigen or portions thereof may be incorporated in DNA constructs, usually self-replicating construct, capable of introduction to and expression in in vitro cell culture. Usually, the DNA constructs will be capable of replication in a unicellular host, such as bacteria or yeast, but may also be intended for introduction to and the integration within the genome of cultured mammalian or other eukaryotic cell lines. DNA constructs prepared for introduction into bacteria usually include replication system recognized by the host, the desired coding sequence for the 79 kD antigen or a portion thereof, transcriptional and translational initiation regulatory sequences joined to the 5'-end of the antigen coding sequence, and transcriptional and translational termination regulatory sequences drawing to the 3'-end of the antigen coding sequence. The transcriptional regulatory sequences will typically include a heterologous promoter which is recognized by the host. Conveniently, available expression vectors which include the replication system and transcriptional and translational regulatory sequences together with an insertion site for the antigen coating region may be employed.

The present invention further provides polypeptides which correspond to the 79 kD antigen or a fragment thereof. The polypeptides will usually be either haptenic or antigenic, typically including at least six amino acids, usually including at least nine amino acids, and more usually at least twelve amino acids found contiguously within a natural form of the 79 kD antigen. The contiguous amino acids may be located within any regions of the antigen. Longer peptides up to and including substantially the full length of the natural protein, and larger, may also find use.

Usually, the polypeptides will define or correspond to at least one determinant site (also known as epitopic site) which is characteristic of a naturally-occurring 79 kD antigen of *Borrelia burgdorferi*. By characteristic, it is meant that the determinant site will allow immunologic detection of the exposed polypeptide segment in a biological sample with reasonable assurance, in most cases allowing the *Borrelia burgdorferi* to be immunologically distinguished from other related organisms, particularly pathogenic organisms.

The polypeptides will be useful as a reagents for use in diagnostic methods and kits, for preparing polyclonal and monoclonal antibodies, and for use as the immunogenic component in vaccine compositions. Each of these uses will be described in more detail hereinafter.

In a preferred aspect, the polypeptides of the present invention will be identical to or equivalent to at least a portion of the amino acid sequence set forth in SEQ ID NO: 2. By equivalent, it is meant that a substantial identity of amino acids exist over a series of at least 10 contiguous residues, or that each position of the corresponding sequences is either identical to or has conservative substitution in at least about 60% of the residues, preferably at least about 70% of the residues, and more preferably at least about 80% of the residues. The polypeptide sequences, however, may be modified by occasional deletions, additions, or replacements in accordance with known methods for comparison. See, for example, *Sequence Analysis Software Package,* University of Wisconsin Biotechnology Center, Madison, Wis. Conservative substitutions or replacements within the groups (a) gly, ala; (b) val, ile, leu; (c) asp, glu; (d) asn, gin; (e) ser, thr; (f) lys, arg; and (g) phe, tyr.

Synthetic polypeptides which are immunologically cross-reactive with a natural 79 kD antigen may be produced by either of at least two general approaches. First, polypeptides having fewer than about 100 amino acids, more usually having fewer than about 50 amino acids, can be synthesized by the Merrifeld solid-phase synthesis method where amino acids sequentially added to a growing chain. See, Merrifield (1963) Journal of the American Chemical Society J. Am. Chem. Soc. 85: 2149–2146. Conveniently, the amino acid sequences may be taken directly from the listing in FIG. 4. Equipment for automatically synthesizing polypeptides is commercially available from suppliers such as Applied Biosystems, Inc., Foster City, Calif.; DuPont Company, Biotechnology Systems, Wilmington, Del.; and MilliGen/Biosearch, a division of Millipore, Burlington, Mass.

An alternative for synthesizing polypeptides of the present invention involves the expression in cultured cells of recombinant DNA molecules encoding the 79 kD antigen or a desired portion thereof. The gene itself may be natural or synthetic, as described above. The natural gene is obtainable from cDNA or genomic libraries using standard techniques. In particular, probes synthesized based on the nucleotide sequence of SEQ ID NO: 1 may be used to identify and isolate genes representing other alleles of the 79 kD antigen gene using well known methods.

To be useful in the detection and therapeutic methods of the present invention, the polypeptides are usually obtained in substantially pure form. That is, the polypeptides will be at least about 50% pure by weight and be substantially free of interfering proteins and contaminants. Preferably, the polypeptides of the present invention will be isolated or synthesized to a purity of at least about 80% by weight, more preferably being at least about 95% by weight or greater. Using conventional protein purification techniques, homogeneous polypeptide compositions of at least 99% by weight can be obtained. For example, the polypeptides may be purified by use of the antibodies described hereinafter in affinity chromatography procedures. Such affinity chromatography is performed by first linking antibodies to a solid support and then contacting the solid support with the source of the polypeptides, e.g. lysates of the *Borrelia burgdorferi* which naturally produce the 79 kD antigen or lysates of cultured cells in which the 79 kD antigen or fragment thereof have been recombinantly produced.

Production of antibodies to the approximately 79 kD antigen of *Borrelia burgdorferi* or antigenic portions thereof may be accomplished using the purified or synthetic polypeptides of the present invention. Once a sufficient quantity of the polypeptide has been obtained by any of the methods described above, polyclonal antibodies specific for the determinant regions may be produced in in vivo or in vitro techniques. In vivo techniques rely on the exposure of antigenic polypeptides or fragments to any of a wide variety of vertebrates, suitable vertebrates are typically non-human, such as mice, rats, rabbits, sheep, goats, and the like. Polypeptides having at least about 5 amino acids, usually at least about 30 amino acids, and preferably at least about 50 amino acids may serve directly as immunogens. If the polypeptide is smaller than about 10 kD, particularly smaller than about 6 kD, it may be necessary to join the polypeptide to a larger molecule to elicit the desired immune response. The immunogens are then injected into the animal host according to a predetermined schedule, and the animals are bled periodically, with successive bleeds generally having improved titer and specificity. Such antisera will then be purified in order to produce the desired monospecific antibodies of the present invention. Conveniently, purification can be accomplished by affinity chromatography using the polypeptides of the present invention coupled to a suitable solid phase. Such affinity chromatography for the purification of antibodies is well described in the patent and scientific literature. See, for example, Hudson and Hay, *Practical Immunology,* Blackwell Scientific Publications, Oxford, 1980, the relevant portions of which are incorporated herein by reference. Suitable in vitro techniques for producing the monospecific antibodies of the present invention involve the in vitro exposure of lymphocytes to the antigenic polypeptides corresponding the 79 kD antigen of *Borrelia burgdorferi.* Such techniques produce monoclonal antibodies and are described in Huse et al. (1989) *Science* 246: 1275–1281; and Ward et al. (1989) Nature 341: 544–546, both of which are incorporated herein by reference.

Monoclonal antibodies may also be prepared by the now classic technique of Kohler and Milstein, as well as by improvements on their basic technique. Briefly, these methods rely on preparing immortalized cell lines capable of producing antibodies having the desired specificity, i.e., reactivity with the determinant regions of the 79 kD antigen. Such immortalized cell lines may be produced by a variety of techniques. Conveniently, a small vertebrate, such as mouse, is hyperimmunized with the desired antigen by the method just described in connection with the preparation of polyclonal antibodies. The vertebrate is then killed, usually several days after the final immunization, the spleen removed, and the spleen cells immortalized. The manner of immortalization is not critical. Presently, the most common technique is fusion with a myeloma cell fusion partner, as first described by Kohler and Milstein (1976) Eur. J. Immunol. 6: 511–519. Other techniques include EVB transformation, transformation with bare DNA, e.g., oncogenes, retroviruses, and the like, and any other method which provides for the stable maintenance of the cell line and production of monoclonal antibodies. Common techniques are described in Lane and Harlow, *Antibodies: A Laboratory Manual,* Cold Spring Harbor Press, New York, 1988; and Goding, *Monoclonal Antibodies: Principles and Practice,* 2nd Edition, Academic Press, New York, 1986, both of which are incorporated herein by reference.

When employing fusion with a fusion partner, the manner of fusion is usually not critical and various techniques may be employed. Conveniently, the spleen cells and myeloma cells are combined in the presence of a nonionic detergent, usually polyethylene glycol, and other additives such as Dulbecco's Modified Eagle's Medium, for a few minutes. At the end of the fusion, the nonionic detergent is rapidly moved by washing the cells. The fused cells are promptly dispensed in small culture wells (usually in a microtiter plate) at relatively low density, ranging from about 1 to $5 \times 10^5$ per well, in a selective medium chosen to support growth of the hybrid cells while being lethal to the myeloma cells. Usually, the myeloma cell line has been mutated to be sensitive to a lethal agent, typically being HAT sensitive. After a sufficient time, usually from about 1 to 2 weeks, colonies of hybrids are observed and plates containing hybrid positive wells are identified. The plates and wells having only one colony per well are selected, and supernatants from these wells are tested for binding activity against the desired 79 kD antigen or isolated portion thereof. Once positive hybridomas are identified, the cell line can be maintained as a viable culture and/or by lyophilization and frozen storage.

Depending on the desired use for the antibodies, further screening of the hybridomas may be desirable. Hybridomas providing high titers are desirable. Furthermore, cytotoxic antibodies, e.g., IgG$_2$b, IgG$_3$ and IgM, may be selected for use in therapeutic treatment of *Borrelia burgdorferi* infection. For use in immunodiagnostic assays as described in more detail hereinbelow, antibodies having very high specificity for corresponding determinants are desirable.

Once the desired hybridomas have been selected, monoclonal antibodies may be isolated from the supernatants of the growing colonies. The yield of antibodies obtained, however, is usually low. The yield may be enhanced by various techniques, such as injection of the hybridoma cell line into the peritoneal cavity of a vertebrate host which will accept the cells. Monoclonal antibodies may then be harvested from the ascites fluid or the blood. Proteinaceous and other contaminants will usually be removed from the monoclonal antibodies prior to use by conventional techniques, e.g., chromatography, gel filtration, precipitation, extraction, or the like.

By properly selecting the polypeptides used as the immunogen, antibodies having high specificity and affinity for the desired 79 kD antigen epitope can be obtained. The polypeptide selected should represent one or more epitopic sites which are unique to the antigen protein and which can distinguish *Borrelia burgdorferi* from closely related pathogens and other potentially cross-reactive proteins. Such unique epitopes are found on polypeptides expressed by cells containing sequences disclosed in SEQ ID NO: 2.

The polypeptides and antibodies of the present invention may be used with or without modification. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescers, chemiluminescers, magnetic particles, biotin, and the like. Patents teaching the use of such labels include U.S. Pat. Nos. 3,817,837; 3,850,752; 3,939,350; 3,996,345; 4,277,437; 4,275,149; and 4,366,241, the disclosures of which are incorporated herein by reference.

Antibodies and polypeptides prepared as described above can be used in various immunological techniques for detecting the 79 KD antigen of *Borrelia burgdorferi* in biological specimens, particularly body fluid samples, including blood, plasma, serum, urine, stool, and the like as well as cell samples, such as tissue biopsy samples. The use of blood, plasma and serum samples will preferably be preferred.

A first type of immunoassay will involve combining the patient sample with monospecific antibody, either polyclonal or monoclonal, which is capable of specifically binding to the 79 kD antigen in the sample. The antibody will usually be labeled or immobilized, as described above, and detection of binding between the antibody and antigen will be indicative of the presence of *Borrelia burgdorferi* in the sample. Numerous specific protocols are available for performing such antibody-based immunoassays and are well described in the scientific and patent literature. Such protocols can generally be classified as heterogeneous (requiring separation of the antigen from a sample) or homogenous (not requiring separation); competitive or noncompetitive; and the like.

A second type of immunoassays relies on the combination of the patient sample with the isolated 79 kD antigen polypeptide or a fragment thereof. The polypeptide will be able to bind to a patient antibody which has been produced in response to infection with *Borrelia burgdorferi*. The specific protocols for detecting patient antibody with the polypeptides will generally rely on use of immobilized polypeptide to capture and remove the antibody from the sample. The captured antibody can be detected in using labeled anti-human antibody in a sandwich technique or using a labeled polypeptide in a semi-competitive technique.

An exemplary polypeptide-based assay for detecting infection by *Borrelia burgdorferi* is an enzyme linked immunosorbent assay (ELISA) where the polypeptide is immobilized on a solid phase, usually a test well in a microtiter plate, although polystyrene beads, glass beads, agarose beads, and other solid phases may also find use. After exposure to sample and binding of antibody (if one is present) the solid phase is exposed to labeled antibody directed against the patient antibody, e.g. labeled anti-human antibody. The label is an enzyme which may be detected by exposure to appropriate substrates. Such ELISA techniques are amply described in the patent and scientific literature.

Of course, numerous other assay protocols exist which may combine use of the polypeptide antigens and antibodies of the present invention. The above descriptions of polypeptide-based and antibody-based assays are intended to be exemplary only.

In addition to immunoassays, the presence of *Borrelia burgdorferi* in a patient sample may be detected using nucleic acid hybridization probes prepared as described hereinabove. The samples will be treated to release chromosomal DNA from any *Borrelia burgdorferi* which may be present in the sample. Optionally, but not necessarily, the patient sample may be cultured to expand the amount of *Borrelia burgdorferi* present prior to treatment to release the chromosomal DNA. In a first particular protocol, the *Borrelia burgdorferi* will be lysed to free the chromosomal DNA, and the released DNA fixed on a solid phase support. The DNA is denatured so that single stranded fragments remain on the solid phase, and the solid phase is contacted with the labeled oligonucleotide probes of the present invention under hybridizing conditions. The hybridizing conditions are sufficiently stringent to assure binding specificity. Hybridization of the nucleic acid probes to the solid phase is thus diagnostic of the presence of the *Borrelia burgdorferi*. Such nucleic acid hybridization methods are described in U.S. Pat. No. 4,358,535, the disclosure of which is incorporated herein by reference.

An alternative protocol permits the *Borrelia burgdorferi* to be lysed in a liquid phase without prior culturing to expand the amount of the microorganisms present. Lysing is effected using a detergent to free the nucleic acids under denaturing conditions. The lysed solution is then contacted with the solid phase which selectively binds a single strand of nucleic acids which may then be detected using the oligonucleotide probes of the present invention. Such an alternative protocol described in PCT application Ser. No. 86/00139, the disclosure of which is incorporated herein by reference. Methods for performing such nucleic acid hybridization assays are described in general in Hanes and Higgins, *Nucleic Acid Hybridization: A Practical Approach,* IRL Press, 1985, the disclosure of which is incorporated herein by reference.

The use of hybridization assays may be combined with polymerase chain reaction techniques to amplify any amount of a gene encoding the 79 kD antigen which may be present in the patient sample. Polymerase chain reaction employ pairs of nucleotides, usually from about 10 to 50 nucleotides in length, and which are spaced from about 50 to 500 nucleotides apart on either of the two complementary strands of the 79 kD gene. Specimen preparation will include cellular lysis, typically followed by separation of the released nucleic acids on a solid phase, usually for example, glass beads or silicone particles such as those employed in the commercial kit GENECLEAN, available from Bio101, La Jolla, Calif. After the single stranded nucleic acids are bound to the solid phase, they can be amplified by thermal cycling in the presence of the nucleotide primers and DNA polymerase. Typically, the temperature will be cycled between about 98° C. and 60° C., for time periods as short as 1 or 2 minutes per cycle. Cycling can be continued for as long as the desire to achieve amplification of a portion of the gene bounded by the two primers. The amplified gene fragment may then be detected using labeled oligonucleotide probes generally as described above.

Vaccines against *Borrelia burgdorferi* infections may be prepared using the compositions of the present invention. These vaccines may be passive, consisting of Ig supplementation which interferes with *Borrelia burgdorferi* growth or toxicity. Alternatively, vaccines may be active producing a humoral and/or cellular response providing protective immunity by active suppression of *Borrelia burgdorferi* infections.

A vaccine prepared utilizing the 79 kD polypeptide antigen or immunogenic equivalents will usually comprise: (a) fixed cells either recombinantly altered to produce these antigen proteins or cells from the *Borrelia burgdorferi* itself; (b) a crude cell extract; or (c) a partially or completely purified antigen preparation. Fusion proteins combining a segment of the 79 kD antigen will be readily prepared. In some embodiments, a multiple vaccination may be achieved by fusing these antigens with other target antigens on a single protein, inducing protection against multiple infectant vectors. Alternatively, a "cocktail" of different immunogens may be simultaneously administered or inoculated. These immunogens can be prepared in vaccine dose form by well-known procedures. These vaccines can be in the form of an injectable dose and may be administered intramuscularly, intravenously, or subcutaneously. These vaccines can also be administered intranasally by aspiration, or orally by mixing the active components with food or water, providing a tablet form, and the like. Means for administering, or more typically inoculating, these vaccines should be apparent to those skilled in the art from the teachings herein; accordingly, the scope of the invention is not limited to any particular delivery form.

For parenteral administration, such as subcutaneous injection, these immunogens can be combined with a suitable physiologically acceptable carrier, for example, it can be administered in water, saline, alcohol, fats, waxes, or buffered vehicles with or without various adjuvants or immunomodulating agents. Suitable immunological adjuvants or agents include, but are not limited to, aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Proplonobacterium acnes), Bordetolla pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel.

The proportion of immunogen and adjuvant can be varied over a broad range so long as both are present in effective amounts. On a per-dose basis, the amount of the immunogen can range broadly from about 1.0 pg to about 100 mg per kg of host, usually at least about 10 pg, typically at least about 100 pg, and preferably at least about 1 ng per kg of host weight, and usually less than about 1 mg, typically less than about 10 μg, and more typically less than about 1 μg, and preferably less than about 100 ng per kg of host. A preferable range is from about 10 pg to about 100 ng per dose. A suitable dose size will usually be between about 0.01 and 5 ml, preferably about 0.5 ml for a 20–59 kg organism. Comparable dose forms can also be prepared for parenteral administration to smaller or larger patients but the amount of immunogen per dose will usually be smaller, for a smaller patients.

For the initial vaccination of immunologically naive patients, a regiment of between 1 and 4 doses can be used with the injections spaced out over a 2 to 6-week period. Typically, a two-dose regimen is used. The second dose of the vaccine then should be administered some weeks after the first dose, for example, about 2 to 4 weeks later. Patients that have been previously exposed to *Borrelia burgdorferi.*

The vaccine may also be combined with other vaccines for other diseases to produce multivalent vaccines. It may also be combined with other medicaments, for example, antibiotics. A pharmaceutically effective amount of the vaccine can be employed with a pharmaceutically acceptable carrier such as viral capsid protein complex or diluent understood to be useful for the vaccination of animals.

The following examples are offered by way of illustration, not by way of limitation.

EXPERIMENTAL

MATERIALS AND METHODS

Bacterial strains. The isolates used in this study were chosen to represent a wide geographical distribution of *Borrelia burgdorferi* strains. The *Borrelia burgdorferi* isolates Son 335, Son 188, Hum 3336, and Ala 410 were received from M. Bissett (California Department of Public Health, Berkeley, Calif.). Isolates RSL20, CA2, and CA3 were received from R. S. Lane (Department of Entomological Sciences, U. C. Berkeley, Calif.). The *Borrelia burgdorferi* isolates B31 (Bb), B35 (At), Wisconsin, Mass., 297, B914, and K48, *B. hermsii, B. coriaceae* and *B. duttonii* strains were supplied by R. C. Johnson (University of Minnesota, Minneapolis, Minn.). Strain PGU was received from V. Preac-Mursic (University of Munich, Munich). The B56 isolate was received from A. Schonberg (Institute fur Veterinarmedizin des Bundesgesundheitsamtes, West Germany), *B. anserina* strain was obtained from R. Walker (U. C. Davis, Davis, Calif.) (see Table 1). The spirochetes were maintained in BSKII (Barbour-Stoenner-Kelly) medium (Barbour (1984) Yale J. Biol. Med. 57: 521–525) at 33° C. The cells were harvested at mid-logphase of growth ($10^8$/ml), washed in PBS, and prepared for DNA or protein analysis as described below.

TABLE 1

Description of Organisms

| Isolate | Source | Location |
|---|---|---|
| *B. burgdorferi* | | |
| B31 ATCC35210 | *Ixodes dammini* | New York |
| Wis | human skin isolate | Wisconsin |
| Ma | human skin isolate | Massachusetts |
| B35 reference strain | | |
| ATCC35211 | *Ixodes ricinus* | Switzerland |
| K48 | *Ixocdes ricinus* | Czechoslovakia |
| V297 | human cerebral spinal fluid | Connecticut |
| B56 | *Ixodes ricinus* | Germany |
| B914 | *Ixodes ricinus* | Germany |
| P/GU | human skin isolate | Germany |
| California isolates | | County |
| Son335 | *Ixodes pacificus* | Sonoma |
| Son188 | *Ixodes pacificus* | Sonoma |
| Hum3336 | *Ixodes pacificus* | Humboldt |
| Ala410 | *Ixodes pacificus* | Alameda |
| CA2 | *Ixodes neotomae* | Mendocino |
| CA3 | *Ixodes pacificus* | Marin |
| RSL20 | *Ixodes pacificus* | Marin |
| *B. coriaceae* | | |
| ATCC 43381 (B.c.) | *Ornithodoros coriaceae* | California |
| *B. hermsii* | | |
| ATCC 35209 (B.h.) | *Ornithodoros hermsii* | Washington |
| *B. anserina* | poultry | California |
| *B. duttonii* | mouse | Minnesota |

Cloning of the chromosomal DNA from strain B31. Chromosomal DNA was isolated as follows. A 20-ml portion of logarithmic-growth-phase cells was washed three times in phosphate-buffered saline (pH 7.2) plus 5 MM $MgCl_2$. The pellets were suspended in 100 μl of 15% sucrose in 50 mM Tris hydrochloride, pH 8.0–50 mM EDTA, to which an equal volume of 5 M NaCl was added. To this solution was added 1/10 volume (20 μl) of 1% sodium deoxycholate. The solution was placed on ice for 20 minutes, followed by centrifugation in a microcentrifuge for 5 min. (The supernatant fluid, containing the plasmid DNA, was saved for other studies.) The pellet, containing the chromosomal DNA, was suspended in 100 μl of 15% sucrose in 50 mM Tris hydrochloride, pH 8.0–50 mM EDTA. To this was added 50 μl of 100% sodium dodecyl sulfate and 25 μl of 20 mg of proteinase K per ml. The solution was incubated for 30 min at 37° C., followed by phenol extraction and ethanol precipitation. The chromosomal DNA was digested with ClaI and ligated into a ClaI and ligated into a ClaI-digested Pev-Vrf expression vector (Crowl et al. (1985) Gene 38: 31–38). *E. coli* RRI (λ cI857) was transformed with the recombinant plasmids. Expression of cloned genes into this vector was controlled by heat shock (42° C. for 2 h). Recombinant colonies were screened for expression of *Borrelia burgdorferi* antigens by colony blot immunoassay (Craft et al. (1986) Clin. Invest. 78: 934–938). Positive clones were further characterized by immunoblot assay (Burnett (1981) Anal. Biochem. 112: 195–203, Towbin et al. (1979) Proc. Natl. Acad. Sci. USA 76: 4350–4354) by using sodium dodecyl sulfate-polyacrylamide gel electrophoresis (12% gels) (Laemmli (1970) Nature 227: 680–685). Recombinant plasmids from clones identified to be expressing *Borrelia burgdorferi* antigens were purified (Birnbolm (1983) J. Clin. Microbiol. 25: 2296–2301), radiolabeled (Feinberg et al. (1983) Anal. Biochem. 132: 6–13, Maniatis et al. (1982) *Molecular Cloning: A Laboratory Manual,* Cold Spring Harbor Laboratory, Cold Spring Harbor, N.Y.), and used to probe Southern blots (Southern (1975) J. Mol. Biol. 98: 503–518) of pulsed-field gels (Schwartz et al. (1984) Cell 37: 67–75 containing undigested, whole-cell *Borrelia burgdorferi* DNA. The electrophoresis was performed as previously described (LeFebvre et al. (1989) J. Clin. Microbiol. 27: 389–393.

Subcloning and sequencing. The gene expressing the 79.8 kD antigen (LeFebvre et al. (1990) J. Clin. Microbiol. 28: 1673–1675) was determined to be contained within a 2.5 kbp FoKI fragment of the original 6.5 kbp ClaI insert in the pLPI plasmid based on DNA sequence analysis. This fragment was subcloned into a pUC19 plasmid according to standard procedures (Maniatis et al. (1982) supra.) and was designated pLP4. The gene was sequenced according to standard procedures (Sanger et al. (1977) Proc. Natl. Acad. Sci. USA 74: 5463–5467). Within this 2.5 kbp fragment were several HindIII sites. A 500 bp HindIII fragment of the gene was subcloned, radiolabeled (Feinberg et al. (1983) Anal. Biochem. 132: 6–13, Maniatis (1982) supra.), and used as a probe to determine the presence and configuration of the gene in other *Borrelia burgdorferi* isolates from North America and Europe as well as other Borrelia spp.

Amino acid sequence and analysis of the antigen. The amino acid sequence of the antigen, hydrophobic and hydrophilic domains, and codon usage were derived from the nucleic acid sequence using the Genetics Computer Group (GCG) software (Devereux (1989) Version 6.0, Genetics Computer Group, University of Wisconsin, Biotechnology Center, Madison, Wis.).

Detection of the chromosomal gene expressing the 79.8 kD antigen in North American and European isolates. Whole cell DNA from the Borrelia spp. was isolated as previously described (Anderson et al. (1989) J. Clin. Microbiol. 27: 13–20). The purified DNA was digested with ClaI (the restriction enzyme used initially to clone the 79.8 kD gene (LeFebvre et al. (1990) supra.) according to the manufacturer's specifications (BRL). The digested fragments were fractionated in a 0.7% agarose gel at 60 V for 15.5 hr in Tris-Borate buffer (TBE, 0.089 M Tris, 0.089 M boric acid, 0.002 M EDTA, pH8.0). The gel was stained with ethidium bromide and photographed under ultraviolet illumination. The DNA was transferred to a nylon membrane by the method of Southern (Southern (1975) J. Mol. Biol. 47: 61–66). The hybridization and subsequent washes were carried out under stringent conditions according to standard procedures (Maniatis (1982) supra.).

Immunoblot analysis for expression of the 79.8 kD antigen in North American and European isolates. Expression of the 79.8 kD antigen in the *Borrelia burgdorferi* isolates and Borrelia spp. was determined. Sodium-dodecyl-sulfate-polyacrylamide gel electrophoresis (SDS-PAGE) was performed as previously described (Laemmli (1970) Nature 227: 680–685, Maniatis et al. (1982) supra.). Approximately 20 µg of whole cell lysates of each isolate was added to a 12% gel. The gel was run at 60 mA constant current for 4.5–5 hr. Transfer of the electrophoresed proteins to nitrocellulose membranes was performed with a Pharmacia/LKB semi-dry transfer system according to manufacturer's specifications (Pharmacia, Uppsala, Sweden). The membrane was blocked and probed by standard procedures (Maniatis et al. (1982) supra.). Rabbit antiserum raised against *Borrelia burgdorferi* (titered at 1:10,000 by enzyme-linked immunosorbent assay (ELISA)) was used at a dilution of 1:5000 to probe the blot. Biotinylated goat anti-rabbit antibody (Vector Laboratories, Burlingame, Calif.) was added, followed by alkaline phosphatase conjugated to streptavidin (Kirkegaard and Perry Laboratories, Gaithersburg, Md.). The enzyme substrate for the alkaline phosphatase was 5-bromo-4-chloro-3-indolylphosphate.

RESULTS

Cloning of Chromosomal DNA from strain B31.

Of approximately 10 clones which were identified as expressing *Borrelia burgdorferi* antigens in *E. coli* cells, 3 were found to express an 83-kDa protein (later determined to be approximately 79.8 kD), as determined with rabbit polyclonal antiserum raised against whole-cell *Borrelia burgdorferi* (FIG. 1). The protein had the same molecular size and antigenic reactivity as an 83-kDa antigen in *Borrelia burgdorferi* cells. Several lower-molecular-weight antigens were also expressed by the clone. These antigens are not discussed further herein.

FIG. 1 is an immunoblot demonstrating the reactivity of the putative 83-kDa antigen to rabbit antiserum raised against whole-cell *Borrelia burgdorferi*. The whole-cell lysates were fractionated in 12% acrylamide gels prior to transfer to nitrocellulose membranes. Lane 1, *Borrelia burgdorferi* B31; lane 2, *E. coli* RRI (λ cI857) (negative control); lane 3, induced *E. coli* RRI (λ cI857) containing the Pev-Vrf expression vector (negative control); lane 4, *E. coli* RRI (λ cI857) containing a recombinant Pev-Vrf ligated to a randomly cloned piece of *Borrelia burgdorferi* chromosomal DNA; lanes 5 to 7, *E. coli* RRI (λ cI857) induced with recombinants of Pev-Vrf containing *Borrelia burgdorferi* chromosomal DNA inserts expressing the 83-kDa antigen.

Figure 2:
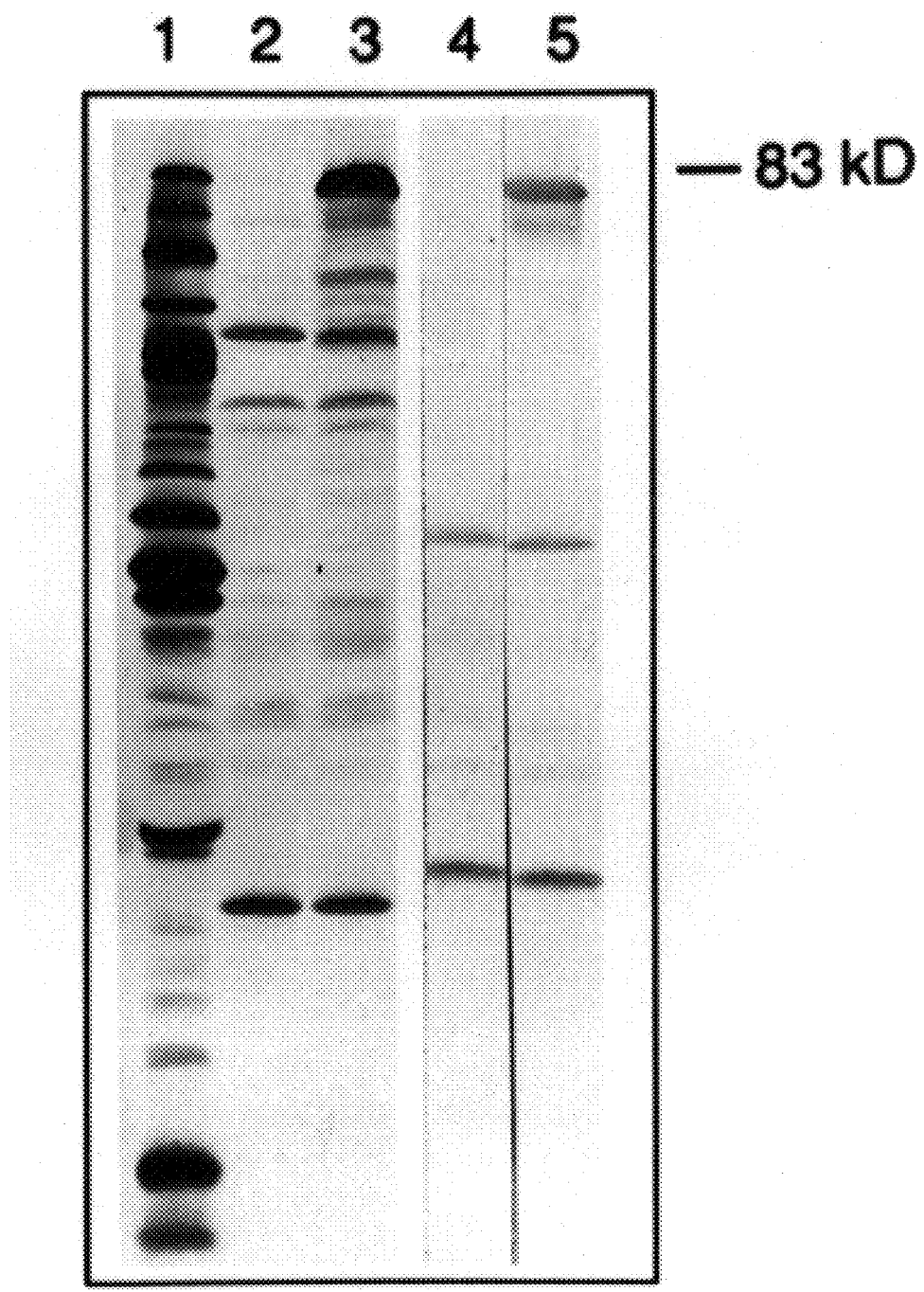
FIG. 2 is an immunoblot demonstrating the reactivity of the approximately 79 kD antigen to human serum from seropositive Lyme borreliosis patients.

One of the recombinant plasmids expressing the putative 83-kDa antigen, designated pLP1, was further characterized. FIG. 2 represents an immunoblot of lysed whole-cell *Borrelia burgdorferi* and *E. coli* cells transformed with either pLP1 or pUC18 plasmids. The blot was exposed to human antisera from two patients presenting with symptoms of Lyme borreliosis and determined to have been exposed to the agent by using enzyme-linked immunosorbent assay (Voller et al. (1980) *Manual of Clinical Immunology*, 2nd Ed., American Society for Microbiology, Washington, D.C.) with sera diluted 1:200 (data not shown). The 83-kDa antigen expressed in the *E. coli* cells containing the pLP1 plasmid reacted with the sera from both patients. No reaction at this molecular size was seen in the pUC18 control cells. These results demonstrate the fact that the 83-kDa antigen expressed by the cloned chromosomal gene in *E. coli* represents a major antigen of *Borrelia burgdorferi* which induces an immune response in the human host. No reaction to the antigen was observed with antisera from humans who served as negative controls (data not shown).

The immunoblot of FIG. 2 demonstrates the reactivity of the putative 83-kDa antigen to human serum from seropositive Lyme borreliosis patients. Lanes 1 to 3 were reacted with serum from patient A, and lanes 4 and 5 were reacted with patient B antiserum. Lane 1, *B. burgdorferi* B31 whole cells; lanes 2 and 4, *E. coli* RRI (λ cI857) induced with the Pev-Vrf expression vector (negative control); lanes 3 and 5, *E. coli* RRI (λ cI857) transformed with the recombinant plasmid pLP1 expressing the 83-kDa antigen.

Figure 3A:
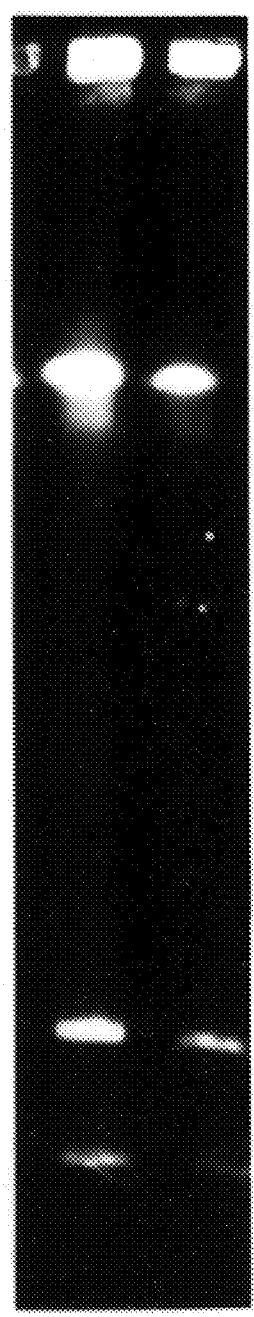
FIG. 3A is a polyacrylamide gel of whole-cell *Borrelia burgdorferi*.
Figure 3B:
FIG. 3B is a Southern blot of the gel in FIG. 3A.

FIG. 3A is a photograph of an ethidium bromide-stained pulsed-field gel illuminated by UV irradiation. Several bands, representing linear and circular plasmids as well as chromosomal DNA, are evident. Of importance in this figure is the largest band which entered the gel (-l.c.) and the DNA remaining in the loading well. These two regions represent broken or linearized chromosomal DNA and intact circular chromosomal DNA, respectively. As demonstrated hereinafter, both of these bands represent chromosomal DNA of *Borrelia burgdorferi*. FIG. 3B is an autoradiograph demonstrating the results of a Southern blot hybridization of this gel. The probe used in lane 1 was labeled whole-cell B31 DNA. Radiolabeled recombinant plasmid pLP1 (Maniatis et al. (1982) supra.) was used as the probe in lane 2. The pLP1 probe hybridized specifically and exclusively to the two bands representing *Borrelia burgdorferi* chromosomal DNA, as described above. Thus, pLP1 represents the first description of a chromosomal gene expressing an antigen in *Borrelia burgdorferi*. Only *B. coriaceae* has been shown to encode major antigens in chromosomal DNA (Perng et al. (1990) Infect. Immun. 58: 1744–1748). All other reports describing antigen expression in Borrelia species have located the genes on linear plasmids (Barbour (1988) J. Clin. Microbiol. 26: 475–478; Barbour et al. (1987) Science 237: 409–411; Howe et al. (1986) Infect. Immun. 54: 207–212; Howe et al. (1984) Science 227: 645–646; Meier et al. (1985) Cell 41: 403–409; and Plasterk et al. (1985) Nature 318: 257–262).

FIG. 3A is an ethidium bromide-stained pulsed-field gel of whole-cell *Borrelia burgdorferi* B31 DNA, cc., Circular chromosomal DNA which did not enter the gel; l.c. broken or linearized chromosomal DNA. FIG. 3B is a Southern blot of the gel in FIG. 3A. Lane 1 was probed with radiolabeled whole-cell B31 DNA. Lane 2 was probed with the recombinant plasmid pLP1 containing the 83-kDa antigen gene.

DNA and amino acid sequence. The gene expressing the 79.8 kD antigen was determined to be contained within the 2.5 kbp ClaI fragment in the original pLP1 clone. The gene was sequenced and a functional TATA box (Pribnow Box) and ribosome binding site (Shine Dalgarno sequence) were identified (SEQ ID NO: 1). SEQ ID NO: 1 lists the DNA sequence of the gene, and SEQ ID NO: 2 lists the amino acid sequence of the expressed antigen. The hydrophobicity profile revealed that the 79.8 kD protein is a hydrophilic protein (78%). Two large hydrophobic domains were identified; one located at the carboxy-terminal portion (about 30 amino acid residues), and the other at the amino terminal portion (about 20 amino acid residues). The central domain of the protein consisted of hydrophilic amino acids (about 350 amino acid residues). On the basis of its amino acid composition, the 79.8 kD protein is an acidic protein with an isoelectric point of 4.92. The calculated molecular mass (79.8 kD) was somewhat lower than the molecular mass estimated from SDS-PAGE (83 kD). No cysteine residues, two tryptophan residues, and three histidine residues were found in the deduced amino acid sequence. In a comparison with previously published protein sequences from a search of a protein data base, a low degree of homology (<15%) was observed. Table 2 lists the codon frequency and amino acid usage for the antigen.

TABLE 2

Codon frequency and amino acid usage in the B31 79.8kDa antigen gene.

| A.A.[a] | Codon | Number[b] | A.A. | Codon | Number |
|---|---|---|---|---|---|
| Gly | GGG | 3 | Thr | ACG | 0 |
| Gly | GGA | 8 | Thr | ACA | 11 |
| Gly | GGT | 10 | Thr | ACT | 13 |
| Gly | GGC | 4 | Thr | ACC | 2 |
| Glu | GAG | 23 | Tyr | TAT | 19 |
| Glu | GAA | 40 | Tyr | TAC | 0 |
| Asp | GAT | 60 | Leu | TTG | 14 |
| Asp | GAC | 8 | Leu | TTA | 31 |
| Val | GTG | 5 | Phe | TTT | 23 |
| Val | GTA | 6 | Phe | TTC | 2 |
| Val | GTT | 30 | Ser | TCG | 0 |
| Val | GTC | 0 | Ser | TCA | 9 |
| Ala | GCG | 0 | Ser | TCT | 23 |
| Ala | GCA | 11 | Ser | TCC | 3 |
| Ala | GCT | 13 | Arg | CGG | 1 |
| Ala | GCC | 3 | Arg | CGA | 1 |
| Ala | GCC | 3 | Arg | CGA | 1 |
| Arg | AGG | 5 | Arg | CGT | 1 |
| Arg | AGA | 12 | Arg | CGC | 0 |
| Ser | AGT | 22 | Gln | CAG | 12 |
| Ser | AGC | 9 | Gln | CAA | 18 |
| Lys | AAG | 28 | His | CAT | 3 |
| Lys | AAA | 63 | His | CAC | 0 |
| ASN | AAT | 40 | Leu | CTG | 1 |
| Asn | AAC | 5 | Leu | CTA | 1 |
| Met | ATA | 9 | Leu | CTT | 21 |
| Ile | ATA | 11 | Leu | CTC | 0 |
| Ile | ATT | 40 | Pro | CCG | 2 |
| Ile | ATC | 2 | Pro | CCA | 3 |
| Cys | TGT | 0 | Pro | CCT | 11 |
| Cys | TGC | 0 | Pro | CCC | 0 |
| End | TAG | 0 | Trp | TGG | 2 |
| End | TAA | 1 | End | TGA | 0 |

[a]A.A.: amino acid.
[b]Number indicates the sum usage of a condon in the 79.8kD antigen gene.

Figure 4:
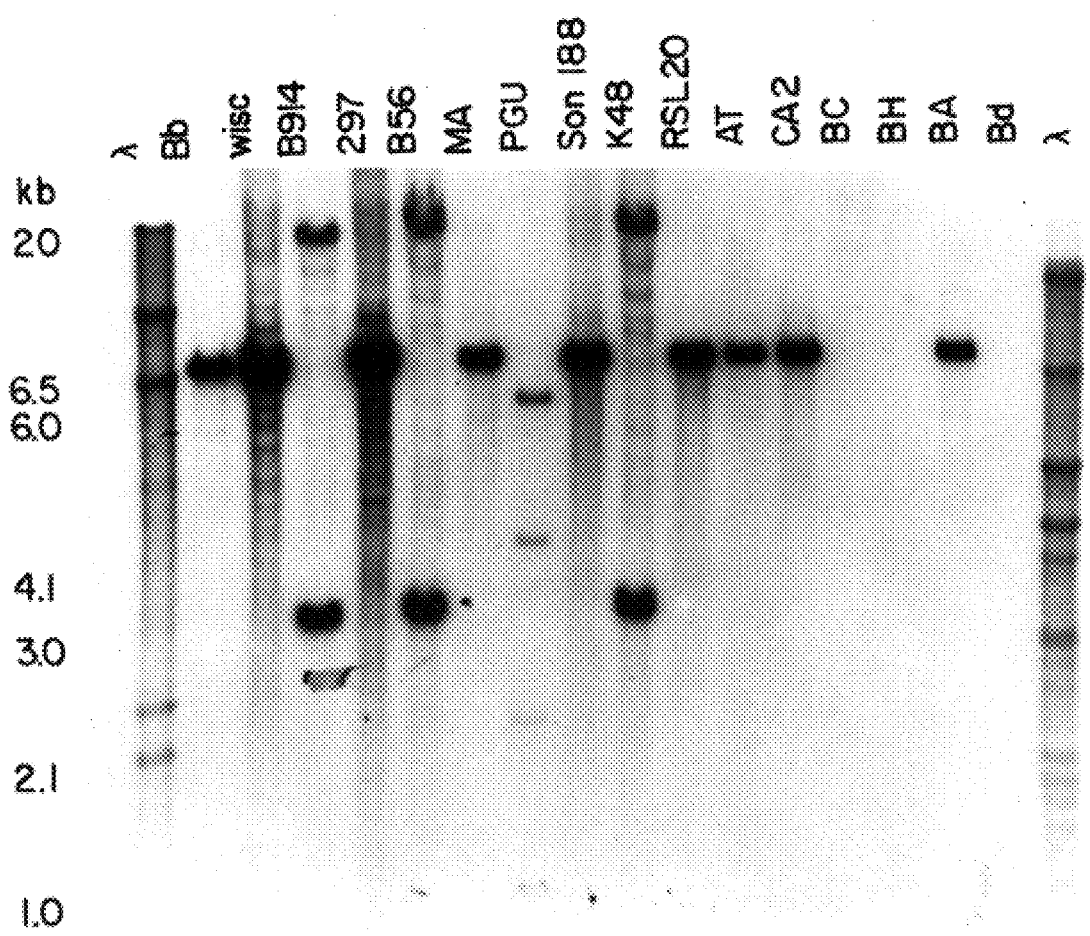
FIG. 4 is an autoradiograph of whole cell DNA from *Borrelia burgdorferi* digested with ClaI and probed with a labeled fragment of the 79.8 kD gene.

Detection of the 79.8 kD antigen gene in *Borrelia burgdorferi* isolates and *Borrelia* spp. Whole cells DNA, digested with ClaI, was electrophoresed, blotted, and probed with the labeled 500 bp subclone of the 79.8 kD protein gene. FIG. 4 displays an autoradiograph of the ClaI digested whole cell DNA hybridized to the probe. A single major band of approximately 6.5 kb was seen in B31, the strain from which the gene was cloned. A single major band of the same size was also observed in the Wisc, 297, MA, Son188, RSL20, AT, and CA2 *Borrelia burgdorferi* isolates and in *B. anserina*.

The B914, B56, and K48 strains were similar to each other in that they revealed 2 major band which hybridized to the probe. The weaker of these 2 bands resolved at 20 kb and the stronger resolved at 3 kb. The P/Gu strain demonstrated 4 band which hybridized to the probe at 6.8, 4.1, 2.1, and 1.0 kbp. The *B. coriaceae, B. hermsii, B. duttoni* did not hybridize to the probe.

Figure 5:
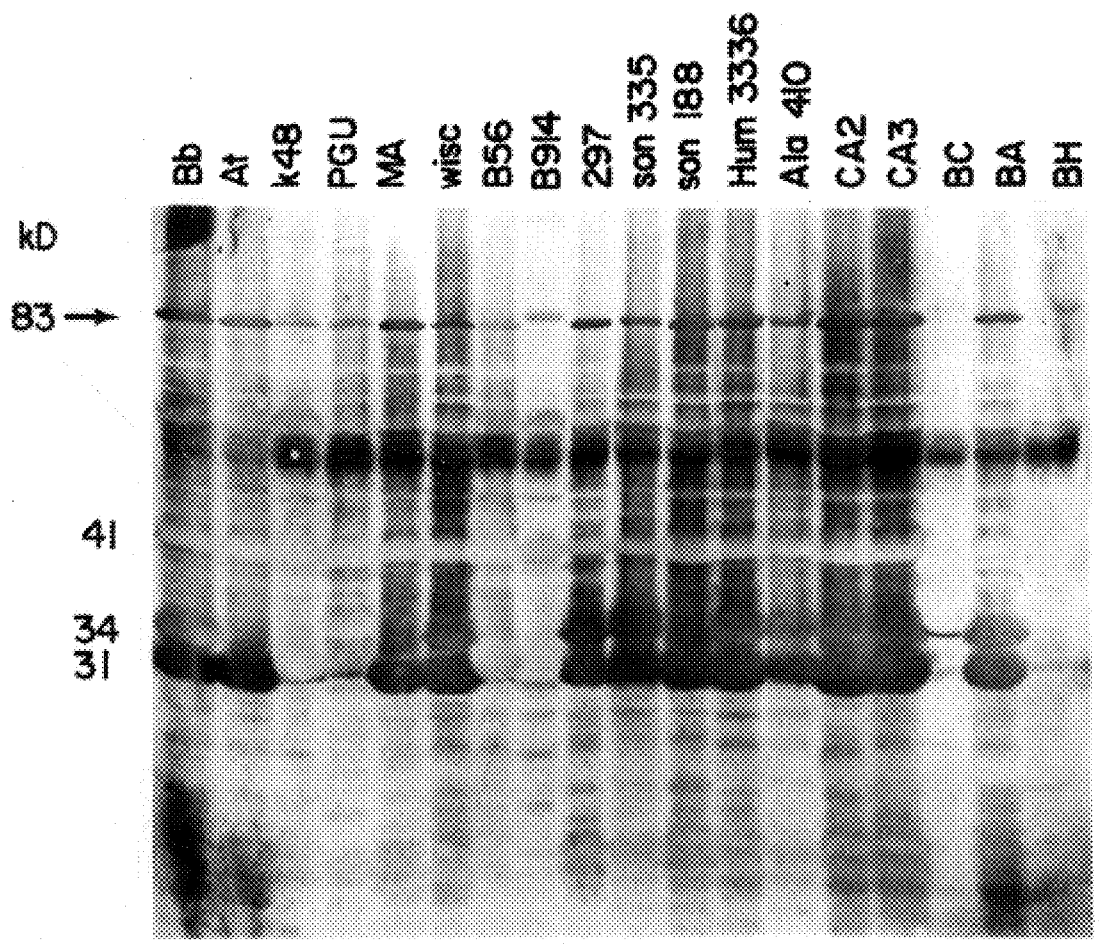
FIG. 5 is an immunoblot of whole cell lysates of representative strains of *Borrelia burgdorferi* reacted with antisera raised against the 79.8 kD antigen.

Immunoassay of *Borrelia burgdorferi* strains and *Borrelia* spp. for expression of the 79.8 kD antigen in vitro. FIG. 5 is an immunoblot of whole cell lysates of representative strains of the *Borrelia burgdorferi* isolates and other Borrelia spp. discussed in Table 1. It is apparent from FIG. 5 that the 79.8 kD antigen is a commonly expressed antigen amongst *Borrelia burgdorferi* isolates. All of the strains assayed exhibited a reacting antigen at approximately 79.8 kD. Previous reports have also identified the presence of this antigen in other *Borrelia burgdorferi* isolates (Craft et al. (1986) supra.; LeFebvre et al. (1990) supra.; LeFebvre et al. (1990) J. Clin. Microbiol. 28: 700–707; Maniatis et al. (1982) supra.; Muhlemann et al. (1982) Lancet i: 553–554; and Nadal et al. (1989) Pediatr. Res. 26: 377–382). The B914 strain exhibited a slightly higher molecular weight antigen. Of the non-*Borrelia burgdorferi* spp., only *B. anserina* expressed a reacting antigen at 79.8 kD. In Coomassie blue or silver stained gels of *Borrelia burgdorferi* the 79.8 kD protein could not be visualized (data not shown) thus suggesting that it is expressed at low levels within the cells. This finding, in turn, indicates that the protein is a potent immunogen based on its low level of expression within *Borrelia burgdorferi* isolates and its strong reactivity to anti-*Borrelia burgdorferi* immune sera.

Although the foregoing invention has been described in detail for purposes of clarity of understanding, it will be obvious that certain modifications may be practiced within the scope of the appended claims.

What is claimed is:

1. An isolated oligonucleotide comprising at least ten contiguous nucleotides which are the same as or complementary to ten contiguous nucleic acids from SEQ ID No.: 1, which oligonucleotide binds under stringent conditions to a chromosomal gene of *Borrelia burgdorferi* which encodes a conserved antigen of approximately 79 kD.

2. An oligonucleotide as in claim 1, further comprising a detectable label.

3. A pair of isolated oligonucleotides comprising sequences of from 10 to 50 nucleotides each, wherein the oligonucleotides have different sequences from each other and wherein each oligonucleotide sequence is the same as or complementary to a pair of contiguous nucleotide sequences in SEQ ID NO.: 1, wherein the contiguous sequences are spaced-apart by from 50 to 500 nucleotides in SEQ ID No.: 1.

4. An isolated nucleic acid sequence as set forth in SEQ ID NO.: 1.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2258 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 51..2151

(xi) SEQUENCE DESCRIPTION: SEQ ID NO:1:

-continued

| | |
|---|---|
| ATTTAGTTGG TAAGGTAGAT TATAATTAAA TTTATAGGAG AATTTCTTTT ATG AAA<br>                                                                                                                                         Met Lys<br>                                                                                                                                          1 | 56 |
| AAA ATG TTA CTA ATC TTT AGT TTT TTT CTT ATT TTC TTG AAT GGA TTT<br>Lys Met Leu Leu Ile Phe Ser Phe Phe Leu Ile Phe Leu Asn Gly Phe<br>       5                            10                           15 | 104 |
| CCT GTT AGT GCA AGA GAA GTT GAT AGG GAA AAA TTA AAG GAC TTT GTT<br>Pro Val Ser Ala Arg Glu Val Asp Arg Glu Lys Leu Lys Asp Phe Val<br>      20                           25                           30 | 152 |
| AAT ATG GAT CTT GAG TTT GTA AAT TAT AAA GGC CCT TAT GAT TCT ACA<br>Asn Met Asp Leu Glu Phe Val Asn Tyr Lys Gly Pro Tyr Asp Ser Thr<br>35                      40                           45                         50 | 200 |
| AAT ACA TAT GAA CAA ATA GTG GGT ATT GGG GAG TTT TTA GCA AGA CCG<br>Asn Thr Tyr Glu Gln Ile Val Gly Ile Gly Glu Phe Leu Ala Arg Pro<br>                55                           60                         65 | 248 |
| TTG ACC AAT TCC AAT AGC AAC TCA AGT TAT TAT GGA AAA TAT TTT ATT<br>Leu Thr Asn Ser Asn Ser Asn Ser Ser Tyr Tyr Gly Lys Tyr Phe Ile<br>                    70                           75                         80 | 296 |
| AAT AGA TTT ATT GAT GAT CAA GAT AAA AAA GCA AGC GTT GAT GTT TTT<br>Asn Arg Phe Ile Asp Asp Gln Asp Lys Lys Ala Ser Val Asp Val Phe<br>                  85                           90                         95 | 344 |
| TCT ATT GGT AGT AAG TCA GAG CTT GAC AGT ATA TTG AAT TTA AGA AGA<br>Ser Ile Gly Ser Lys Ser Glu Leu Asp Ser Ile Leu Asn Leu Arg Arg<br>100                     105                       110 | 392 |
| ATT CTT ACA GGG TAT TTA ATA AAG TCT TTC GAT TAT GAC AGG TCT AGT<br>Ile Leu Thr Gly Tyr Leu Ile Lys Ser Phe Asp Tyr Asp Arg Ser Ser<br>115                     120                     125                    130 | 440 |
| GCA GAA TTA ATT GCT AAG GTT ATT ACA ATA TAT AAT GCT GTT TAT AGA<br>Ala Glu Leu Ile Ala Lys Val Ile Thr Ile Tyr Asn Ala Val Tyr Arg<br>                  135                     140                    145 | 488 |
| GGA GAT TTG GAT TAT TAT AAA GGG TTT TAT ATT GAG GCT GCT TTA AAG<br>Gly Asp Leu Asp Tyr Tyr Lys Gly Phe Tyr Ile Glu Ala Ala Leu Lys<br>                150                     155                     160 | 536 |
| TCT TTA AGT AAA GAA AAT GCA GGT CTT TCT AGG GTT TAT AGT CAG TGG<br>Ser Leu Ser Lys Glu Asn Ala Gly Leu Ser Arg Val Tyr Ser Gln Trp<br>            165                     170                     175 | 584 |
| GCT GGA AAG ACA CAA ATA TTT ATT CCT CTT AAA AAG GAT ATT TTG TCT<br>Ala Gly Lys Thr Gln Ile Phe Ile Pro Leu Lys Lys Asp Ile Leu Ser<br>180                     185                     190 | 632 |
| GGA AAT ATT GAG TCT GAC ATT GAT ATT GAC AGT TTA GTT ACA GAT AAG<br>Gly Asn Ile Glu Ser Asp Ile Asp Ile Asp Ser Leu Val Thr Asp Lys<br>195                     200                     205                    210 | 680 |
| GTG GTG GCA GCT CTT TTA AGT GAA AAT GAA GCA GGT GTT AAC TTT GCA<br>Val Val Ala Ala Leu Leu Ser Glu Asn Glu Ala Gly Val Asn Phe Ala<br>                215                     220                    225 | 728 |
| AGA GAT ATT ACA GAT ATT CAA GGC GAA ACT CAT AAG GCA GAT CAA GAT<br>Arg Asp Ile Thr Asp Ile Gln Gly Glu Thr His Lys Ala Asp Gln Asp<br>                  230                     235                    240 | 776 |
| AAA ATT GAT ATT GAA TTA GAC AAT ATT CAT GAA AGT GAT TCC AAT ATA<br>Lys Ile Asp Ile Glu Leu Asp Asn Ile His Glu Ser Asp Ser Asn Ile<br>                245                     250                    255 | 824 |
| ACA GAA ACT ATT GAA AAT TTA AGG GAT CAG CTT GAA AAA GCT ACA GAT<br>Thr Glu Thr Ile Glu Asn Leu Arg Asp Gln Leu Glu Lys Ala Thr Asp<br>260                     265                     270 | 872 |
| GAA GAG CAT AAA AAA GAG ATT GAA AGT CAG GTT GAT GCT AAA AAG AAA<br>Glu Glu His Lys Lys Glu Ile Glu Ser Gln Val Asp Ala Lys Lys Lys<br>275                     280                     285                    290 | 920 |
| CAA AAG GAA GAG CTA GAT AAA AAG GCA ATA AAT CTT GAT AAA GCT CAG<br>Gln Lys Glu Glu Leu Asp Lys Lys Ala Ile Asn Leu Asp Lys Ala Gln<br>                295                     300                    305 | 968 |

| | | |
|---|---|---|
| CAA AAA TTA GAT TCT GCT GAA GAT AAT TTA GAT GTT CAA AGA AAT ACT | 1016 | |
| Gln Lys Leu Asp Ser Ala Glu Asp Asn Leu Asp Val Gln Arg Asn Thr | | |
| 310 315 320 | | |
| GTT AGA GAG AAA ATT CAA GAG GAT ATT AAC GAA ATT AAC AAG GAA AAG | 1064 | |
| Val Arg Glu Lys Ile Gln Glu Asp Ile Asn Glu Ile Asn Lys Glu Lys | | |
| 325 330 335 | | |
| AAT TTA CCA AAG CCT GGT GAT GTA AGT TCT CCT AAA GTT GAT AAG CAA | 1112 | |
| Asn Leu Pro Lys Pro Gly Asp Val Ser Ser Pro Lys Val Asp Lys Gln | | |
| 340 345 350 | | |
| CTA CAA ATA AAA GAG AGC CTG GAA GAT TTG CAG GAG CAG CTT AAA GAA | 1160 | |
| Leu Gln Ile Lys Glu Ser Leu Glu Asp Leu Gln Glu Gln Leu Lys Glu | | |
| 355 360 365 370 | | |
| ACT GGT GAT GAA AAT CAG AAA AGA GAA ATT GAA AAG CAA ATT GAA ATC | 1208 | |
| Thr Gly Asp Glu Asn Gln Lys Arg Glu Ile Glu Lys Gln Ile Glu Ile | | |
| 375 380 385 | | |
| AAA AAA AGT GAT GAA AAG CTT TTA AAA AGT AAA GAT GAT AAA GCA AGT | 1256 | |
| Lys Lys Ser Asp Glu Lys Leu Leu Lys Ser Lys Asp Asp Lys Ala Ser | | |
| 390 395 400 | | |
| AAA GAT GGT AAA GCC TTG GAT CTT GAT CGA GAA TTA AAT TCT AAA GCT | 1304 | |
| Lys Asp Gly Lys Ala Leu Asp Leu Asp Arg Glu Leu Asn Ser Lys Ala | | |
| 405 410 415 | | |
| TCT AGC AAA GAA AAA AGT AAA GCC AAG GAA GAA GAA ATA ACC AAG GGT | 1352 | |
| Ser Ser Lys Glu Lys Ser Lys Ala Lys Glu Glu Glu Ile Thr Lys Gly | | |
| 420 425 430 | | |
| AAG TCA CAG AAA AGC TTA GGC GAT TTG AAT AAT GAT GAA AAT CTT ATG | 1400 | |
| Lys Ser Gln Lys Ser Leu Gly Asp Leu Asn Asn Asp Glu Asn Leu Met | | |
| 435 440 445 450 | | |
| ATG CCA GAA GAT CAA AAA TTA CCT GAG GTT AAA AAA TTA GAT AGC AAA | 1448 | |
| Met Pro Glu Asp Gln Lys Leu Pro Glu Val Lys Lys Leu Asp Ser Lys | | |
| 455 460 465 | | |
| AAA GAA TTT AAA CCT GTT TCT GAG GTT GAG AAA TTA GAT AAG ATT TTT | 1496 | |
| Lys Glu Phe Lys Pro Val Ser Glu Val Glu Lys Leu Asp Lys Ile Phe | | |
| 470 475 480 | | |
| AAG TCT AAT AAC AAT GTT GGA GAA TTA TCA CCG TTA GAT AAA TCT TCT | 1544 | |
| Lys Ser Asn Asn Asn Val Gly Glu Leu Ser Pro Leu Asp Lys Ser Ser | | |
| 485 490 495 | | |
| TAT AAA GAC ATT GAT TCA AAA GAG GAG ACA GTT AAT AAA GAT GTT AAT | 1592 | |
| Tyr Lys Asp Ile Asp Ser Lys Glu Glu Thr Val Asn Lys Asp Val Asn | | |
| 500 505 510 | | |
| TTG CAA AAG ACT AAG CCT CAG GTT AAA GAC CAA GTT ACT TCT TTG AAT | 1640 | |
| Leu Gln Lys Thr Lys Pro Gln Val Lys Asp Gln Val Thr Ser Leu Asn | | |
| 515 520 525 530 | | |
| GAA GAT TTG ACT ACT ATG TCT ATA GAT TCC AGT AGT CCT GTA TTT TTA | 1688 | |
| Glu Asp Leu Thr Thr Met Ser Ile Asp Ser Ser Ser Pro Val Phe Leu | | |
| 535 540 545 | | |
| GAG GTT ATT GAT CCA ATT ACA AAT TTA GGA ACT CTT CAA CTT ATT GAT | 1736 | |
| Glu Val Ile Asp Pro Ile Thr Asn Leu Gly Thr Leu Gln Leu Ile Asp | | |
| 550 555 560 | | |
| TTA AAT ACT GGT GTT AGC CTT AAA GAA AGC ACT CAG CAA GGC ATT CAG | 1784 | |
| Leu Asn Thr Gly Val Ser Leu Lys Glu Ser Thr Gln Gln Gly Ile Gln | | |
| 565 570 575 | | |
| CGG TAT GGA ATT TAT GAA CGT GAA AAA GAT TTG GTT GTT ATT AAA ATG | 1832 | |
| Arg Tyr Gly Ile Tyr Glu Arg Glu Lys Asp Leu Val Val Ile Lys Met | | |
| 580 585 590 | | |
| GAT TCA GGA AAA GCT AAG CTT CAG ATA CTT GAT AAA CTT GAA AAT TTA | 1880 | |
| Asp Ser Gly Lys Ala Lys Leu Gln Ile Leu Asp Lys Leu Glu Asn Leu | | |
| 595 600 605 610 | | |

-continued

```
AAA GTG GTA TCA GAG TCT AAT TTT GAG ATT AAT AAA AAT TCA TCT CTT          1928
Lys Val Val Ser Glu Ser Asn Phe Glu Ile Asn Lys Asn Ser Ser Leu
            615                 620                 625

TAT GTT GAT TCT AAA ATG ATT TTA GTA GCT GTT AGG GAT AAA GAT AGT          1976
Tyr Val Asp Ser Lys Met Ile Leu Val Ala Val Arg Asp Lys Asp Ser
            630                 635                 640

AGT AAT GAT TGG AGA TTG GCC AAA TTT TCT CCT AAA AAT TTA GAT GAG          2024
Ser Asn Asp Trp Arg Leu Ala Lys Phe Ser Pro Lys Asn Leu Asp Glu
            645                 650                 655

TTT ATT CTT TCA GAG AAT AAA ATT ATG CCT TTT ACT AGC TTT TCT GTG          2072
Phe Ile Leu Ser Glu Asn Lys Ile Met Pro Phe Thr Ser Phe Ser Val
            660                 665                 670

AGA AAA AAT TTT ATT TAT TTG CAA GAT GAG TTT AAA AGT CTA GTT ATT          2120
Arg Lys Asn Phe Ile Tyr Leu Gln Asp Glu Phe Lys Ser Leu Val Ile
675                 680                 685                 690

TTA GAT GTA AAT ACT TTA AAG AAA GTT AAG T AACTTTACAG TTAGATTTAA          2171
Leu Asp Val Asn Thr Leu Lys Lys Val Lys
            695                 700

TTTGTATAAA TCGTTAAAAA ACCAAAAAAG CTAAAAACAA AAGTTTTTTG CTTTTTTAAT        2231

ATTTTTTCGG GATGGTGGGA TTCGAAC                                            2258
```

(2) INFORMATION FOR SEQ ID NO:2:

(i) SEQUENCE CHARACTERISTICS:
        (A) LENGTH: 700 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Lys Met Leu Leu Ile Phe Ser Phe Phe Leu Ile Phe Leu Asn
1                 5                  10                  15

Gly Phe Pro Val Ser Ala Arg Glu Val Asp Arg Glu Lys Leu Lys Asp
                20                  25                  30

Phe Val Asn Met Asp Leu Glu Phe Val Asn Tyr Lys Gly Pro Tyr Asp
            35                  40                  45

Ser Thr Asn Thr Tyr Glu Gln Ile Val Gly Ile Gly Glu Phe Leu Ala
        50                  55                  60

Arg Pro Leu Thr Asn Ser Asn Ser Asn Ser Tyr Tyr Gly Lys Tyr
65                  70                  75                  80

Phe Ile Asn Arg Phe Ile Asp Asp Gln Asp Lys Lys Ala Ser Val Asp
                85                  90                  95

Val Phe Ser Ile Gly Ser Lys Ser Glu Leu Asp Ser Ile Leu Asn Leu
            100                 105                 110

Arg Arg Ile Leu Thr Gly Tyr Leu Ile Lys Ser Phe Asp Tyr Asp Arg
        115                 120                 125

Ser Ser Ala Glu Leu Ile Ala Lys Val Ile Thr Ile Tyr Asn Ala Val
    130                 135                 140

Tyr Arg Gly Asp Leu Asp Tyr Lys Gly Phe Tyr Ile Glu Ala Ala
145                 150                 155                 160

Leu Lys Ser Leu Ser Lys Glu Asn Ala Gly Leu Ser Arg Val Tyr Ser
                165                 170                 175

Gln Trp Ala Gly Lys Thr Gln Ile Phe Ile Pro Leu Lys Lys Asp Ile
            180                 185                 190
```

```
Leu Ser Gly Asn Ile Glu Ser Asp Ile Asp Ile Asp Ser Leu Val Thr
    195                 200                 205

Asp Lys Val Val Ala Ala Leu Leu Ser Glu Asn Glu Ala Gly Val Asn
210                 215                 220

Phe Ala Arg Asp Ile Thr Asp Ile Gln Gly Glu Thr His Lys Ala Asp
225                 230                 235                 240

Gln Asp Lys Ile Asp Ile Glu Leu Asp Asn Ile His Glu Ser Asp Ser
                245                 250                 255

Asn Ile Thr Glu Thr Ile Glu Asn Leu Arg Asp Gln Leu Glu Lys Ala
                260                 265                 270

Thr Asp Glu Glu His Lys Lys Glu Ile Glu Ser Gln Val Asp Ala Lys
            275                 280                 285

Lys Lys Gln Lys Glu Glu Leu Asp Lys Lys Ala Ile Asn Leu Asp Lys
290                 295                 300

Ala Gln Gln Lys Leu Asp Ser Ala Glu Asp Asn Leu Asp Val Gln Arg
305                 310                 315                 320

Asn Thr Val Arg Glu Lys Ile Gln Glu Asp Ile Asn Glu Ile Asn Lys
                325                 330                 335

Glu Lys Asn Leu Pro Lys Pro Gly Asp Val Ser Ser Pro Lys Val Asp
                340                 345                 350

Lys Gln Leu Gln Ile Lys Glu Ser Leu Glu Asp Leu Gln Glu Gln Leu
            355                 360                 365

Lys Glu Thr Gly Asp Glu Asn Gln Lys Arg Glu Ile Glu Lys Gln Ile
    370                 375                 380

Glu Ile Lys Lys Ser Asp Glu Lys Leu Leu Lys Ser Lys Asp Asp Lys
385                 390                 395                 400

Ala Ser Lys Asp Gly Lys Ala Leu Asp Leu Asp Arg Glu Leu Asn Ser
                405                 410                 415

Lys Ala Ser Ser Lys Glu Lys Ser Lys Ala Lys Glu Glu Ile Thr
                420                 425                 430

Lys Gly Lys Ser Gln Lys Ser Leu Gly Asp Leu Asn Asn Asp Glu Asn
    435                 440                 445

Leu Met Met Pro Glu Asp Gln Lys Leu Pro Glu Val Lys Lys Leu Asp
    450                 455                 460

Ser Lys Lys Glu Phe Lys Pro Val Ser Glu Val Glu Lys Leu Asp Lys
465                 470                 475                 480

Ile Phe Lys Ser Asn Asn Asn Val Gly Glu Leu Ser Pro Leu Asp Lys
                485                 490                 495

Ser Ser Tyr Lys Asp Ile Asp Ser Lys Glu Glu Thr Val Asn Lys Asp
                500                 505                 510

Val Asn Leu Gln Lys Thr Lys Pro Gln Val Lys Asp Gln Val Thr Ser
            515                 520                 525

Leu Asn Glu Asp Leu Thr Thr Met Ser Ile Asp Ser Ser Ser Pro Val
    530                 535                 540

Phe Leu Glu Val Ile Asp Pro Ile Thr Asn Leu Gly Thr Leu Gln Leu
545                 550                 555                 560

Ile Asp Leu Asn Thr Gly Val Ser Leu Lys Glu Ser Thr Gln Gln Gly
                565                 570                 575

Ile Gln Arg Tyr Gly Ile Tyr Glu Arg Glu Lys Asp Leu Val Val Ile
                580                 585                 590

Lys Met Asp Ser Gly Lys Ala Lys Leu Gln Ile Leu Asp Lys Leu Glu
            595                 600                 605
```

-continued

```
Asn Leu Lys Val Val Ser Glu Ser Asn Phe Glu Ile Asn Lys Asn Ser
    610             615                 620

Ser Leu Tyr Val Asp Ser Lys Met Ile Leu Val Ala Val Arg Asp Lys
625             630                 635                 640

Asp Ser Ser Asn Asp Trp Arg Leu Ala Lys Phe Ser Pro Lys Asn Leu
                645                 650                 655

Asp Glu Phe Ile Leu Ser Glu Asn Lys Ile Met Pro Phe Thr Ser Phe
            660                 665                 670

Ser Val Arg Lys Asn Phe Ile Tyr Leu Gln Asp Glu Phe Lys Ser Leu
        675                 680                 685

Val Ile Leu Asp Val Asn Thr Leu Lys Lys Val Lys
    690                 695                 700
```